US008748650B2

(12) United States Patent
Endo et al.

(10) Patent No.: US 8,748,650 B2
(45) Date of Patent: Jun. 10, 2014

(54) METHOD FOR PRODUCTION OF N-CARBOXY AMINO ACID ANHYDRIDE AND AMINO ACID CARBAMATE COMPOUND

(75) Inventors: Takeshi Endo, Iizuka (JP); Koichi Koga, Iizuka (JP); Atsushi Sudo, Iizuka (JP)

(73) Assignee: JSR Corporation, Tokyo (JP)

( * ) Notice: Subject to any disclaimer, the term of this patent is extended or adjusted under 35 U.S.C. 154(b) by 355 days.

(21) Appl. No.: 13/060,391

(22) PCT Filed: Aug. 26, 2009

(86) PCT No.: PCT/JP2009/004118
§ 371 (c)(1),
(2), (4) Date: Feb. 23, 2011

(87) PCT Pub. No.: WO2010/023892
PCT Pub. Date: Mar. 4, 2010

(65) Prior Publication Data
US 2011/0152561 A1    Jun. 23, 2011

(30) Foreign Application Priority Data

Aug. 29, 2008  (JP) ................ 2008-220862
Oct. 31, 2008  (JP) ................ 2008-282277
Mar. 4, 2009   (JP) ................ 2009-050170

(51) Int. Cl.
*C07C 205/00* (2006.01)

(52) U.S. Cl.
USPC ........................................................ 560/29

(58) Field of Classification Search
USPC .................... 560/29; 562/888, 400
See application file for complete search history.

(56) References Cited

U.S. PATENT DOCUMENTS 5,308,736 A * 5/1994 Defieuw et al. ............ 430/200
2006/0104908 A1 5/2006 Grimmond et al.
2007/0015932 A1 1/2007 Fujita et al.

FOREIGN PATENT DOCUMENTS

| JP | 2004 269414 | 9/2004 |
|---|---|---|
| WO | WO 03/099274 A1 | 12/2003 |
| WO | WO 2004/054674 A2 | 7/2004 |
| WO | WO2008/033328 A2 | 3/2008 |

OTHER PUBLICATIONS

Niu et al. (Solid-Phase Synthesis of Larger Peptides by a New Strategy of Detachment from the Resin, Shanghai Institute of Biochemistry, Academia Sinica, Shanghai 200031, China, Biopolymers, vol. 20, 1833-1843 (1981), pp. 1833-1843).*

Niu et al. (Solid-Phase Synthesis of Larger Peptides by a New Strategy of Detachment from the Resin, Shanghai Institute of Biochemistry, Academia Sinica, Shanghai 200031, China, Biopolymers, vol. 20, 1833-1843 (1981), pp. 1833-1843).*

Zerangue et al. (Interaction of L-cysteine with a human excitatory amino acid transporter, Journal of Physiology, 493.2, pp. 419-423, 1996).*

Endo et al. (Phosgene-Free Synthesis of N-Carboxyanhydrides of a-Amino Acids Based on Bisarylcarbonates as Starting Compounds, Journal of Polymer Science: Part A: Polymer Chemistry, vol. 45, 5365-5369, 2007).*

Extended European Search Report issued Nov. 17, 2011, in Patent Application No. 09809548.2.

Jeremy R. Duvall, et al., "Structure Reassignment and Synthesis of Jenamidines $A_1/A_2$, Synthesis of (+)-NP25302, and Formal Synthesis of SB-311009 Analogues", Journal of Organic Chemistry, vol. 71, No. 22, XP002662116, Oct. 27, 2006, pp. 8579-8590.

Tae Bo Sim, et al., "N-Trityl-and N-Phenylfluorenyl-N-carboxyanhydrides and Their Use in Dipeptide Synthesis", Journal of Organic Chemistry, vol. 64, No. 7, XP002662117, Mar. 11, 1999, pp. 2532-2536.

John Halstrom, et al., "N-Protected N-Carboxyanhydrides IX. Synthesis of N-Aralkyl α-Amino Acid N-Carboxyanhydrides by Carbonyl Insertion with Bis(N-Succinimidyl) Carbonate", Acta Chemica Scandinavica, Series B: Organic Chemistry and Biochemistry, vol. 40, No. 6, XP002662118, 1986, pp. 462-465.

Gerard Barcelo, et al., "Alkyl 1-Chloroalkyl Carbonates: Reagents for the Synthesis of Carbamates and Protection of Amino Groups", Synthesis, vol. 1986, No. 8, XP002662119, Aug. 1986, pp. 627-632, 1123.

Block, H. et al., "N-Carboxy-N-Trityl-a- Amino-Acid Anhydrides in Peptide Synthesis", Peptides, Proc. European Symp. 5th, Oxford, pp. 83-87 (1962).

Yamaguchi, J. et al., "Condensation of α-Amino Acid With Amine in the Absence of a Coupling Agent", Chemistry Letters, vol. 32, No. 9, pp. 830-831 (2003).

Chen, J. et al., "An Improved Large Scale Synthesis of the Schollkopf Chiral Auxiliaries: (2R)- and (2S)-2, 5-Dihydro-3, 6-Dimethoxy-2-Isopropylpyrazine", Organic Process Research & Development, vol. 9, pp. 185-187 (2005).

International Search Report Issued Oct. 27, 2009 in PCT/JP09/004118 filed Aug. 26, 2009.

Office Action in corresponding Japanese Application No. 2010-526541 dated Jan. 21, 2014.

\* cited by examiner

*Primary Examiner* — Brandon Fetterolf
*Assistant Examiner* — Blaine G Doletski
(74) *Attorney, Agent, or Firm* — Oblon, Spivak, McClelland, Maier & Neustadt, L.L.P.

(57) ABSTRACT

A method for production of an N-carboxy amino acid anhydride with efficiency is provided. The method for production of an N-carboxy amino acid anhydride includes a step of reaction of an amino acid organic salt compound with a carbonic acid diester.

20 Claims, No Drawings

METHOD FOR PRODUCTION OF N-CARBOXY AMINO ACID ANHYDRIDE AND AMINO ACID CARBAMATE COMPOUND

FIELD OF THE INVENTION

The present invention relates to methods for production of an N-carboxy amino acid anhydride and an amino acid carbamate compound useful as intermediate raw materials for obtaining polypeptides.

BACKGROUND OF THE INVENTION

N-carboxy amino acid anhydrides are useful as intermediate raw materials for synthesis of polypeptides from amino acids.

A large number of production methods for production of the N-carboxy amino acid anhydrides have been publicly known. The inventors of the present invention have recently found that an amino acid carbamate compound obtained from an amino acid or an ester thereof and diphenyl carbonate is useful as a raw material for synthesis of an N-carboxy amino acid anhydride, and have patent-applied (Patent Document 1).

PATENT DOCUMENT

[Patent Document 1] JP-A-2007-22932

SUMMARY OF THE INVENTION

Problems to be Solved by the Invention

Objects of the present invention is to provide a novel method for production of the above-mentioned N-carboxy amino acid anhydride and a novel method for production of an amino acid carbamate compound.

Means for Solving the Problems

The inventors of the present invention have investigated a novel method for production of an N-carboxy amino acid anhydride. As a result of focusing on an amino acid organic salt compound containing an amino acid as a constituent ion, the inventors have found that a carbonic acid diester may be reacted with the amino acid organic salt compound to provide an amino acid carbamate compound which is useful as a raw material for synthesis of an N-carboxy amino acid anhydride under a moderate condition within a short time period with efficiency, and that the resultant amino acid carbamate compound may be easily cyclized to provide the N-carboxy amino acid anhydride. Accordingly, the inventors have completed the present invention.

The present invention relates to provision of a method for production of an N-carboxy amino acid anhydride, the method including the step of reaction of an amino acid organic salt compound with a carbonic acid diester, and of a method for production of an amino acid carbamate compound, the method including reaction of an amino acid organic salt compound with a carbonic acid diester.

Advantageous Effects of the Invention

According to the present invention, an N-carboxy amino acid anhydride and an amino acid carbamate compound can be produced under a moderate condition within a short time period in industrial scale.

DETAILED DESCRIPTION OF THE INVENTION

Methods of the present invention are a method for production of an amino acid carbamate compound and a method for production of an N-carboxy amino acid anhydride, the both methods are characterized in that these methods include a reaction of an amino acid organic salt compound with a carbonic acid diester. Specifically, the methods include a reaction of an amino acid organic salt compound represented by a formula (1) which contains an amino acid as a constituent ion with a carbonic acid diester represented by a formula (2) to provide an amino acid carbamate compound represented by a formula (A) and a method including dehydrating the resultant amino acid carbamate compound by a known method described in, for example, above-described JP-A-2007-22932 to provide an N-carboxy amino acid anhydride (B) as represented by the following reaction scheme.

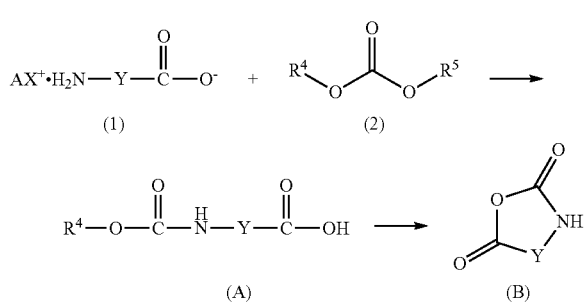

In the formula (1), $AX^+$ represents an organic onium ion and Y represents a divalent hydrocarbon group which may have substituent(s), and in the formula (2), $R^4$ and $R^5$ each independently represent a monovalent hydrocarbon group which may have substituent(s).

In the formula (1), X preferably represents an atom of an element belonging to Group 14, an element belonging to Group 15, an element belonging to Group 16, or an element belonging to Group 17. A tin atom is preferred as the atom of an element belonging to Group 14. Examples of the atom of an element belonging to Group 15 include a nitrogen atom, a phosphorus atom, an arsenic atom, an antimony atom, and a bismuth atom. Of those, a nitrogen atom or a phosphorus atom is preferred. Further, examples of the atom of an element belonging to Group 16 include an oxygen atom, a sulfur atom, a selenium atom, a tellurium atom, and a polonium atom. Of those, an oxygen atom or a sulfur atom is preferred. In addition, examples of the atom of an element belonging to Group 17 include a fluorine atom, a chlorine atom, a bromine atom, an iodine atom, and an astatine atom. Of those, an iodine atom is preferred.

That is, X preferably represents a nitrogen atom, a phosphorus atom, an oxygen atom, a sulfur atom, or an iodine atom in order that a target product may be obtained in high yield. Of those, a nitrogen atom, a phosphorus atom, or a sulfur atom is even more preferred.

It should be noted that, when X represents a tin atom, $AX^+$ represents a stannonium ion, preferably a tertiary stannonium ion. When X represents a nitrogen atom, $AX^+$ represents an ammonium ion, preferably a quaternary ammonium ion. When X represents a phosphorus atom, $AX^+$ represents a phosphonium ion, preferably a quaternary phosphonium ion. When X represents an arsenic atom, $AX^+$ represents an arsonium ion, preferably a quaternary arsonium ion. When X represents an antimony atom, $AX^+$ represents a stibonium ion, preferably a quaternary stibonium ion. When X represents an oxygen atom, $AX^+$ represents an oxonium ion, preferably a tertiary oxonium ion. When X represents a sulfur atom, $AX^+$ represents a sulfonium ion, preferably a tertiary sulfonium ion. When X represents a selenium atom, $AX^+$ represents a selenonium ion, preferably a tertairy selenonium ion. When X reprensets an iodine atom, $AX^+$ represents an iodonium ion, preferably a secondary iodonium ion.

In addition, $AX^+$ in the formula (1) preferably represents (a) a cation represented by $(R^1)_n X^+$ (where $R^1$'s, which are identical to or different from each other, each represent a monovalent hydrocarbon group which may have substituent(s), and n represents an integer of 2 to 4), (b) a cation in which one hydrogen atom or one hydrocarbon group which may have substituent(s) is bonded onto an X atom of a heterocyclic ring containing one or more X atoms which may have substituent(s), or (c) the cation (a) or (b) bonded to a polymer.

In addition, when $AX^+$ represents the cation represented by $(R^1)_n X^+$, X more preferably represents a nitrogen atom or a phosphorus atom. When $AX^+$ is a cation in which one hydrogen atom or one alkyl group which may have substituent(s) is bonded onto an X atom of a heterocyclic ring containing one or more X atoms which may have substituent(s), X more preferably represents a nitrogen atom or a sulfur atom.

Examples of the "monovalent hydrocarbon group which may have substituent(s)" represented by $R^1$ in $(R^1)_n X^+$ include an alkyl group which may have substituent(s), a cycloalkyl group which may have substituent(s), an alkenyl group which may have substituent(s), a cycloalkenyl group which may have substituent(s), an aryl group which may have substituent(s), and an arylalkyl group which may have substituent(s). Of those, an alkyl group which may have substituent(s) is preferred in order that a target product may be obtained in high yield.

Examples of a group which can substitute each of the hydrocarbon groups include: alkoxy groups such as a methoxy group, an ethoxy group, an isopropoxy group, and a tert-butoxy group; a silyl group; tri-substituted silyl groups such as a trimethylsilyl group, a triethylsilyl group, a t-butyl dimethylsilyl group, and a triphenylsilyl group; halogen atoms such as chlorine and fluorine; alkenyl groups such as a vinyl group, an allyl group, a 1-propenyl group, and an iso-propenyl group; alkoxycarbonyl groups such as a methoxycarbonyl group and an ethoxycarbonyl group; an amino group; N,N-disubstituted amino groups such as an N, N-dimethyl amino group and an N,N-diethyl amino group; a hydroxy group; a siloxy group; substituted siloxy groups such as a methyl siloxy group and an ethyl siloxy group; and a cyano group.

Further, in the above-mentioned "alkyl group which may have substituent(s)", examples of the "alkyl group" include an alkyl group having 1 to 20 carbon atoms. An alkyl group having 1 to 15 carbon atoms is preferred and an alkyl group having 1 to 12 carbon atoms is even more preferred. Examples of the alkyl group include a linear or branched alkyl group. Specifically, a methyl group, an ethyl group, an n-propyl group, an isopropyl group, an n-butyl group, an isobutyl group, a sec-butyl group, a tert-butyl group, an n-pentyl group, an n-hexyl group, an n-heptyl group, an n-octyl group, an n-nonyl group, an n-decanyl group, and the like are included. Of those, an n-butyl group is more preferred.

In the above-mentioned "cycloalkyl group which may have substituent(s)", examples of the "cycloalkyl group" include a cycloalkyl group having 3 to 20 carbon atoms. A cycloalkyl group having 3 to 10 carbon atoms is more preferred. Specifically, a cyclopropyl group, a cyclopentyl group, and a cyclohexyl group are included.

In the above-mentioned "alkenyl group which may have substituent(s)", examples of the "alkenyl group" include an alkenyl group having 2 to 18 carbon atoms. An alkenyl group having 2 to 10 carbon atoms is even more preferred. Specifically, a vinyl group, a propenyl group, a 3-butenyl group, and the like are included.

In the above-mentioned "cycloalkenyl group which may have substituent(s)", examples of the "cycloalkenyl group" include a cycloalkenyl group having 5 to 18 carbon atoms. A cycloalkenyl group having 5 to 10 carbon atoms is even more preferred. Specifically, a cyclohexenyl group, a cyclooctenyl group, a cyclododecenyl group, and the like are included.

In the above-mentioned "aryl group which may have substituent(s)", examples of the "aryl group" include an aryl group having 6 to 14 carbon atoms. An aryl group having 6 to 10 carbon atoms is even more preferred. Specifically, a phenyl group, a tolyl group, a naphthyl group, and the like are included.

In the above-mentioned "arylalkyl group which may have substituent(s)", examples of the "arylalkyl group" include an arylalkyl group having 7 to 13 carbon atoms. An arylalkyl group having 7 to 9 carbon atoms is even more preferred. Specifically, a benzyl group, a phenethyl group, a naphthylmethyl group, a naphthylethyl group, and the like are included.

In addition, n in $(R^1)_n X^+$ represents an integer of 2 to 4. When X represents an atom of an element belonging to Group 14, n=3. When X represents an atom of an element belonging to Group 15, n=4. When X represents an atom of an element belonging to Group 16, n=3. When X represents an atom of an element belonging to Group 17, n=2.

Preferred specific examples of the cation represented by $(R^1)_n X^+$ include: quaternary ammonium ions such as tetrapropylammonium, tetrabutylammonium, tetrapentylammonium, tetrahexylammonium, tetraoctylammonium, trimethylphenylammonium, trimethylbenzylammonium, and triethylbenzylammonium; quaternary phosphonium ions such as tetrabutylphosphonium and butyltriphenylphosphonium; tertiary oxonium ions such as triethyloxonium and tirmethyloxonium; tertiary sulfonium ions such as (2-carboxyethyl)dimethylsulfonium, (3-chloropropyl)diphenylsulfonium, cyclopropyldiphenylsulfonium, diphenyl(methyl)sulfonium, tri-n-butylsulfonium, tri-p-tolylsulfonium, triethylsulfonium, trimethylsulfonium, and triphenylsulfonium; and secondary iodonium ions such as diphenyliodonium. Of those, tetrabutylammonium, tetrabutylphosphonium, and butyltriphenylphosphonium are more preferred.

The "heterocyclic ring containing one or more X atoms" in the above-mentioned "cation in which one hydrogen atom or one hydrocarbon group which may have substituent(s) is bonded onto an X atom of a heterocyclic ring containing one or more X atoms which may have substituent(s)" is preferably an aromatic heterocyclic ring or an unsaturated heterocyclic ring. When X represents a nitrogen atom, the heterocyclic ring is preferably an aromatic heterocyclic ring, more preferably a five- or six-membered ring having 1 to 3 nitrogen atoms, or a fused ring containing any such ring. When X represents a sulfur atom, the heterocyclic ring is preferably a five- or six-membered ring having 1 or 2 sulfur atoms, or a fused ring containing any such ring.

In addition, as in the case of $R^1$ described above, examples of the "hydrocarbon group which may have substituent(s)" bonded onto an X atom of the heterocyclic ring containing X atoms in the above-mentioned "cation in which one hydrogen atom or one hydrocarbon group which may have substituent(s) is bonded onto an X atom of a heterocyclic ring containing one or more X atoms which may have substituent(s)" include an alkyl group which may have a substituent, a cycloalkyl group which may have substituent(s), an alkenyl group which may have substituent(s), a cycloalkenyl group which may have substituent(s), an aryl group which may have substituent(s), and an arylalkyl group which may have substituent(s). The alkyl group which may have substituent(s) is preferably an alkyl group having 1 to 6 carbon atoms, more preferably a linear or branched alkyl group having 1 to 6 carbon atoms. Specific examples of such group include a methyl group, an ethyl group, an n-propyl group, an isopropyl group, an n-butyl group, an isobutyl group, an sec-butyl group, a tert-butyl group, an n-pentyl group, and an n-hexyl group. Of those, a methyl group and an ethyl group are preferred.

In addition, an X atom except the X atom that forms the cation and a carbon atom in the heterocyclic ring containing X atoms in the above-mentioned "cation in which one hydrogen atom or one hydrocarbon group is bonded onto an X atom of a heterocyclic ring containing one or more X atoms" may each have on itself a substituent such as an alkyl group, a halogen atom, an alkoxy group, a nitro group, or a cyano group. Here, the alkyl group is preferably a linear or branched alkyl group having 1 to 12 carbon atoms, and the alkoxy group is preferably an alkoxy group having 1 to 6 carbon atoms.

In the above-mentioned "cation in which one hydrogen atom or one hydrocarbon group is bonded onto an X atom of a heterocyclic ring containing one or more X atoms", when X represents a nitrogen atom, more preferred specific examples of the heterocyclic cation include pyrrolium, imidazolium, 2H-pyrrolium, pyrazolium, pyridinium, pyrazinium, pyrimidinium, pyridazinium, indolizinium, indolium, 3H-indolium, 1H-indazolium, isoindolium, purinium, 4H-quinolizinium, isoquinolinium, quinolinium, phthalazinium, naphthyridinium, quinoxalinium, quinazolinium, cinnolinium, pteridinium, 4aH-carbazolium, carbazolium, β-carbolinium, phenanthridinium, acridinium, perimidinium, phenanthrolinium, and phenazinium. Of those, imidazolium, pyridinium, and pyrrolidinium are preferred, and imidazolium is more preferred. Further, when X represents an oxygen atom, more preferred specific examples of the heterocyclic cation include 2,4,6-trimethylpyrylium and 2,6-di-tert-butyl-4-methylpyrylium. In addition, when X represents a sulfur atom, more preferred specific examples of the heterocyclic cation include 1,3-benzodithiolium and 1-benzyltetrahydrothiophen-1-ium.

When X in the above-mentioned "cation in which one hydrogen atom or one hydrocarbon group is bonded onto an X atom of a heterocyclic ring containing one or more X atoms" represents a nitrogen atom, the heterocyclic cation is more preferably, for example, a cation represented by any one of the following formulae (4) to (8). Of those, a cation represented by the formula (4) is even more preferred.

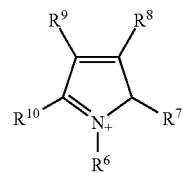

(4)

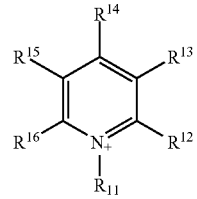

(5)

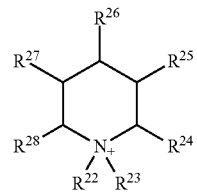

(6)

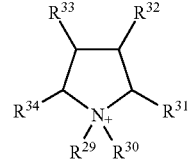

(7)

(8)

(In the formula, $R^6$ to $R^{34}$ each independently represent a hydrogen atom or a hydrocarbon group which may have substituent(s).)

Of a hydrogen atom and a hydrocarbon group which may have substituent(s) each represented by any one of $R^6$ to $R^{34}$, the "hydrocarbon group which may have substituent(s)" is, for example, an alkyl group which may have substituent(s), a cycloalkyl group which may have substituent(s), an alkenyl group which may have substituent(s), a cycloalkenyl group which may have substituent(s), an aryl group which may have substituent(s), or an arylalkyl group which may have substituent(s) as in the case of $R^1$ described above. The alkyl group which may have substituent(s) is preferably an alkyl group having 1 to 20 carbon atoms, more preferably an alkyl group having 1 to 12 carbon atoms such as a methyl group, an ethyl group, or a propyl group.

The heterocyclic cation in the above-mentioned "cation in which one hydrogen atom or one alkyl group is bonded onto an X atom of a heterocyclic ring containing one or more X atoms" is more preferably, for example, a cation represented by any one of the following formulae (41) to (43). Of those, a cation represented by the formula (41) is even more preferred.

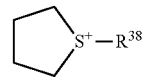

(41)

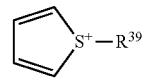

(42)

(43)

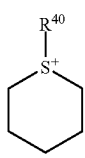

Of a hydrogen atom and an alkyl group which may have substituent(s) each represented by any one of $R^{38}$ to $R^{40}$, the "alkyl group" is preferably an alkyl group having 1 to 20 carbon atoms, more preferably an alkyl group having 1 to 12 carbon atoms such as a methyl group, an ethyl group, a propyl group, or a butyl group.

That is, preferred specific examples of the above-mentioned "cation in which one hydrogen atom or one alkyl group is bonded onto an X atom of a heterocyclic ring containing one or more X atoms" include cations represented by the following formulae (9) to (39), (44), and (45). Of those, the cations represented by the formulae (9), (10), (12), (13), (16), (17), (44), and (45) are more preferred, and the cations represented by the formulae (9), (16), and (45) are even more preferred.

(9)

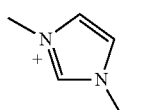

(10)

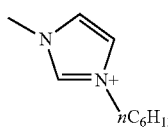

(11)

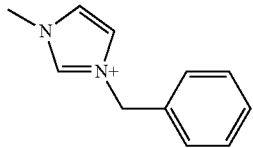

(12)

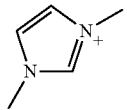

(13)

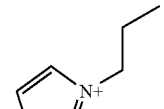

(14)

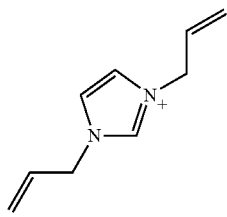

(15)

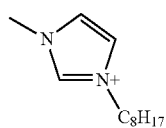

(16)

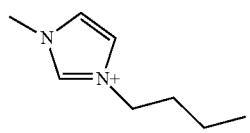

(17)

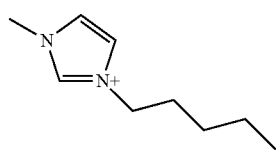

(18)

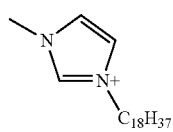

(19)

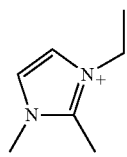

(20)

(21)

(22)

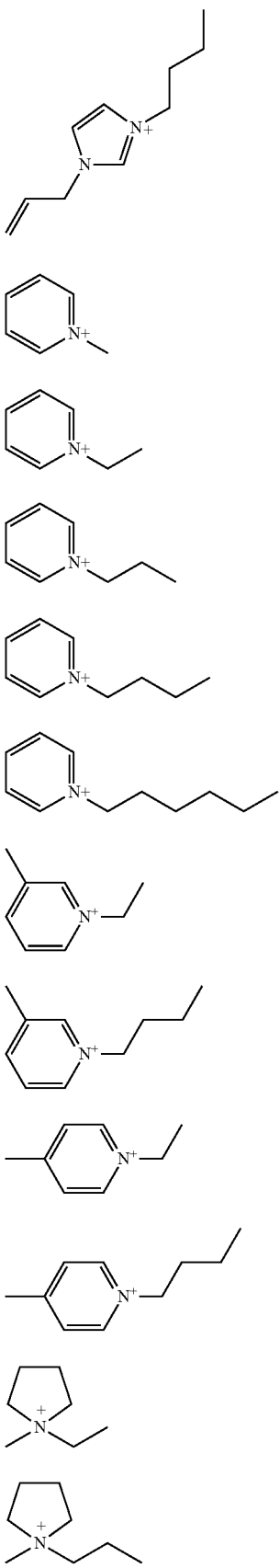
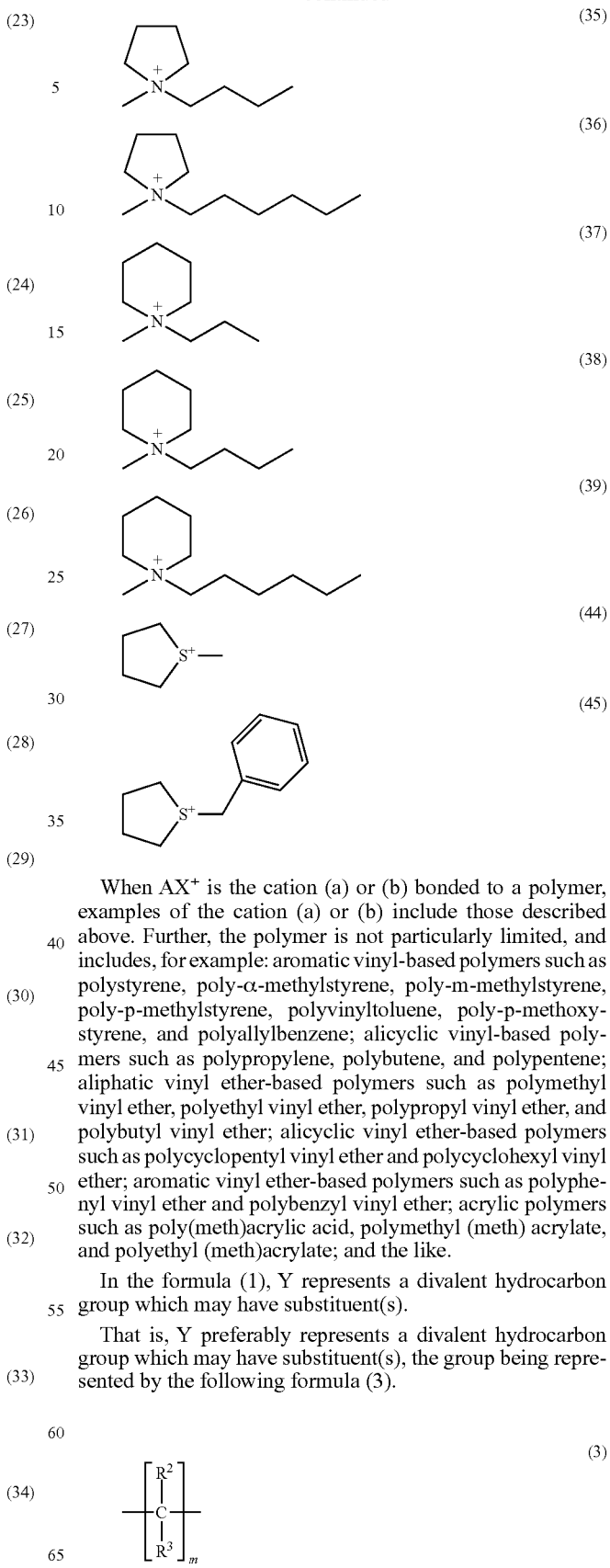

When AX⁺ is the cation (a) or (b) bonded to a polymer, examples of the cation (a) or (b) include those described above. Further, the polymer is not particularly limited, and includes, for example: aromatic vinyl-based polymers such as polystyrene, poly-α-methylstyrene, poly-m-methylstyrene, poly-p-methylstyrene, polyvinyltoluene, poly-p-methoxystyrene, and polyallylbenzene; alicyclic vinyl-based polymers such as polypropylene, polybutene, and polypentene; aliphatic vinyl ether-based polymers such as polymethyl vinyl ether, polyethyl vinyl ether, polypropyl vinyl ether, and polybutyl vinyl ether; alicyclic vinyl ether-based polymers such as polycyclopentyl vinyl ether and polycyclohexyl vinyl ether; aromatic vinyl ether-based polymers such as polyphenyl vinyl ether and polybenzyl vinyl ether; acrylic polymers such as poly(meth)acrylic acid, polymethyl (meth) acrylate, and polyethyl (meth)acrylate; and the like.

In the formula (1), Y represents a divalent hydrocarbon group which may have substituent(s).

That is, Y preferably represents a divalent hydrocarbon group which may have substituent(s), the group being represented by the following formula (3).

$$\left[ \begin{array}{c} R^2 \\ | \\ C \\ | \\ R^3 \end{array} \right]_m \quad (3)$$

(In the formula, $R^2$ and $R^3$ each independently represent a hydrogen atom or a monovalent hydrocarbon group which may have substituent(s), and m represents an integer of 1 to 15.)

In the formula (3), $R^2$ and $R^3$ each independently represent a hydrogen atom or a monovalent hydrocarbon group which may have substituent(s), and examples of the monovalent hydrocarbon group which may have substituent(s) include an alkyl group which may have substituent(s), a cycloalkyl group which may have substituent(s), an aryl group which may have substituent(s), an arylalkyl group which may have substituent(s), a heterocyclic group which may have substituent(s), and a heterocyclic alkyl group which may have substituent(s). Examples of a group which can substitute each of the hydrocarbon groups include: halogen atoms such as chlorine and fluorine; a phenyl group; a hydroxy group; a mercapto group; an amino group; a carboxy group; an ester group; an alkoxycarbonyl group; and an aralkyloxycarbonyl group.

The above-mentioned alkyl group which may have substituent(s) in each of $R^2$ and $R^3$ refers to an alkyl group in which any part of the alkyl group may be substituted. Preferred specific examples of the alkyl group include a methyl group, an ethyl group, an n-propyl group, an isopropyl group, an n-butyl group, an isobutyl group, a sec-butyl group, a tert-butyl group, a trichloroethyl group, an adamantyl group, a methylmercaptoethyl group, a hydroxymethyl group, a hydroxyethyl group, a mercaptomethyl group, a mercaptoethyl group, a methylmercaptoethyl group, a carboxymethyl group, a carboxyethyl group, an aminopropyl group, an aminobutyl group, an aminocarbonylmethyl group, an aminocarbonylethyl group, a pentyl group, a heptyl group, an octyl group, $—(CH_2)_3—NH—C(=NH)—NH_2$, and $—(CH_2)_3NH—CO—NH_2$.

Further, the cycloalkyl group which may have substituent(s) refers to a cycloalkyl group in which a part of the cycloalkyl group may be substituted. Preferred specific examples of the cycloalkyl group include a cyclopropyl group, a cyclopropyl methyl group, a cyclobutyl group, a cyclopentyl group, a cyclohexyl group, a cyclohexyl methyl group, a cycloheptyl group, and a cyclooctyl group.

Further, the aryl group which may have substituent(s) refers to an aryl group in which any part of the aryl group may be substituted. Preferred specific examples of the aryl group include a phenyl group, a tolyl group, a methoxy phenyl group, a benzyl oxy phenyl group, an ethyl phenyl group, a chloro phenyl group, a fluoro phenyl group, a hydroxy phenyl group, and a nitro phenyl group.

Further, the arylalkyl group which may have substituent(s) refers to an arylalkyl group in which apart of the arylalkyl group may be substituted. Preferred specific examples of the arylalkyl group include a fluorenylmethyl group, a benzyl group, a nitrobenzyl group, an aminobenzyl group, a bromobenzyl group, a methoxybenzyl group, a hydroxybenzyl group, a dihydroxybenzyl group, a phenacyl group, a methoxyphenacyl group, a cinnamyl group, and a phenethyl group.

Further, the heterocyclic group which may have substituent(s) refers to a heterocyclic group in which a part of the heterocyclic group may be substituted. Preferred specific examples of the heterocyclic group include a tetrahydropyranyl group, a tetrahydrofuranyl group, a tetrahydrothienyl group, a piperidyl group, a morpholinyl group, a piperazinyl group, a pyrrolyl group, a pyrrolidinyl group, a furyl group, a thienyl group, a pyridyl group, a furfuryl group, a thenyl group, a pyrimidyl group, a pyrazyl group, an imidazoyl group, an indolyl group, an isoquinolyl group, a quinolyl group, and a thiazolyl group.

In addition, the heterocyclic alkyl group which may have substituent(s) refers to a heterocyclic alkyl group in which a part of the heterocyclic alkyl group may be substituted. Preferred specific examples of the heterocyclic alkyl group include a pyridylmethyl group, an imidazoylmethyl group, and an indolylmethyl group.

Further, as for $R^2$ and $R^3$, any one of $R^2$ and $R^3$ preferably represents a hydrogen atom and the other of $R^2$ and $R^3$ preferably represents a hydrogen atom, the alkyl group which may have substituent(s), the arylalkyl group which may have substituent(s), or the heterocyclic alkyl group which may have substituent(s).

In addition, m represents preferably 1 to 10, more preferably 1 to 8, even more preferably 1.

That is, preferred specific examples of the anion represented by $H_2N—Y—COO^-$ in the formula (1) include anions of α-amino acids as main components of a protein such as an amino acid selected from L-leucine, L-phenylalanine, L-isoleucine, glycine, L-glutamic acid, L-valine, L-aspartic acid, L-tryptophan, L-alanine, L-arginine, L-asparagine, L-cysteine, L-glutamine, L-histidine, L-lysine, L-methionine, L-serine, L-threonine, and L-tyrosine. There are also given anions of, for example, orthinine, norleucine, selenocysteine, and cystein sulfonic acid. Further, anions of, for example, a β-amino acid and a γ-amino acid d may be used depending on intended purposes.

In addition, when the amino acid organic salt compound has a hydroxyl group or thiol group, or a plurality of carboxyl groups or amino groups, a group except that involved in the reaction is preferably protected. Although a method for the protection is not particularly limited, in the case of a hydroxyl group or thiol group, the method is, for example, a method involving substitution with a methyl group or the like. In the case of a carboxyl group, the method is, for example, a method involving substitution with a methyl group, an ethyl group, a benzyl group, a t-butyl group, or the like. In the case of an amino group, the method is, for example, a method involving substitution with a carbobenzyloxy group, a t-butoxycarbonyl group, a benzoyl group, an acetyl group, or the like.

In addition, the amino acid organic salt compound represented by the formula (1) can be produced by the following method. For example, when an amino acid organic salt compound in which $AX^+$ as a cation moiety is a cation represented by $(R^1)_nX^+$ is produced, the compound is obtained by reaction of a hydroxy compound of the cation represented by $(R^1)_nX^+$ and an amino acid in an organic solvent.

Further, a commercially available hydroxy compound can be used as the hydroxy compound of the cation represented by $(R^1)_nX^+$. Specifically, tetrapropylammonium hydroxide, tetrabutylammonium hydroxide, tetrapentylammonium hydroxide, tetrahexylammonium hydroxide, tetraoctylammonium hydroxide, trimethylphenylammonium hydroxide, trimethylbenzylammonium hydroxide, triethylbenzylammoniumhydroxide, tetrabutylphosphoniumhydroxide, trimethylsulfonium hydroxide, and the like are included.

Examples of the organic solvent include: amide-based solvents such as dimethylacetamide, dimethylformamide, and N-methylpyrrolidone; sulfoxide-based solvents such as dimethylsulfoxide; ketone-based solvents such as 2-butanone, methyl ethylketone, and acetone; ester-based solvents such as ethylacetate and butyl acetate; nitrile-based solvents such as acetonitrile; halogen-based solvents such as chloroform and dichloromethane; ether-based solvents such as tetrahydrofuran and cyclopentane monomethyl ether; and alcohol-based solvents such as methanol, ethanol, and butanol.

It should be noted that the reaction is preferably performed in the presence of a dehydrating agent. Examples of the dehydrating agent include: synthetic zeolites such as molecular sieve 4A, molecular sieve 3A, and molecular sieve 5A; anhydrous sodium sulfate; anhydrous magnesium sulfate; and anhydrous calcium sulfate. It should be noted that a condition for the reaction upon production of the amino acid organic salt compound is not particularly limited. The reaction, which can be typically performed in the air, is desirably performed under an inert gas atmosphere such as argon or nitrogen. It should be noted that the reaction can be performed under any one of normal pressure, reduced pressure, and increased pressure. In addition, a reaction temperature is desirably selected from the range of typically −70° C. to 120° C., preferably −10° C. to 100° C. A required reaction time is typically 0.1 to 100 hours.

The amino acid organic salt compound represented by the formula (1) can be produced by a known method as well. As described in, for example, JP-A-2004-269414, the compound is obtained by: dissolving a halogenated product of AX$^+$ as the cation moiety in an aqueous solvent; passing the solution through, for example, an anion exchange resin to exchange the solution for a hydroxy compound; adding an amino acid serving as an anion moiety H$_2$N—Y—COO$^-$ to the compound; and allowing the compound to react with the amino acid. More specifically, a desired amino acid organic salt compound can be produced by: dissolving 1 part by mass of a halogenated product of AX$^+$ in an aqueous solvent; passing the solution through an anion exchange resin to transform the solution into a hydroxy compound; adding about 1 to 1.1 parts by mass, preferably about 1.0 part by mass, of an amino acid represented by H$_2$N—Y—COOH to the compound; stirring the resultant mixed solution under ice cooling; removing the solvent under reduced pressure; and removing an unreacted amino acid from the residue by a proper method.

In addition, when AX$^+$ is the cation (a) or (b) bonded to a polymer, the amino acid organic salt compound is obtained by: dissolving a halogenated product of AX$^+$ as the cation moiety, which is obtained by reaction of a polymer having a halogenated alkyl group such as a chloromethylated polystyrene with a precursor for the cation (a) or (b) such as imidazole, pyridine, or pyrrolidine, in a basic aqueous solvent to exchange the halogenated product for a hydroxy compound; adding an amino acid serving as the anion moiety H$_2$N—Y—COO$^-$ to the compound; and allowing the compound to react with the amino acid.

Further, the carbonic acid diester is preferably a carbonic acid diester represented by the following formula (2).

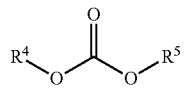
(2)

(In the formula, R$^4$ and R$^5$ each independently represent a monovalent hydrocarbon group which may have substituent(s).)

Examples of the monovalent hydrocarbon group which may have substituent(s) include an alkyl group which may have substituent(s), a cycloalkyl group which may have substituent(s), an alkenyl group which may have substituent(s), a cycloalkenyl group which may have substituent(s), an aryl group which may have substituent(s), and an arylalkyl group which may have substituent(s).

Examples of a group which can substitute each of the hydrocarbon groups include: a nitro group; halogen atoms such as a chlorine atom and a fluorine atom; a perfluoroalkyl group (here, examples of the alkyl group include a linear, branched, or cyclic, saturated or unsaturated alkyl group having 1 to 8 carbon atoms); a perchloroalkyl group (here, examples of the alkyl group include the same as those of the perfluoroalkyl group); an ester group; an acetyl group; a cyano group; and a benzoyl group. A nitro group, a halogen atom, and a halogen-substituted alkyl group (here, examples of the alkyl group include the same as those of the perfluoroalkyl group) are preferred.

In the above-mentioned "alkyl group which may have substituent(s)", examples of the "alkyl group" include an alkyl group having 1 to 20 carbon atoms. An alkyl group having 1 to 10 carbon atoms is even more preferred. Examples of the alkyl group include a linear or branched alkyl group. Specifically, a methyl group, an ethyl group, an n-propyl group, an isopropyl group, an n-butyl group, an isobutyl group, a sec-butyl group, a tert-butyl group, an n-pentyl group, an n-hexyl group, an n-heptyl group, an n-octyl group, an n-nonyl group, an n-decanyl group, and the like are included.

In the above-mentioned "cycloalkyl group which may have substituent(s)", examples of the "cycloalkyl group" include a cycloalkyl group having 3 to 20 carbon atoms. A cycloalkyl group having 3 to 10 carbon atoms is even more preferred. Specifically, a cyclopropyl group, a cyclopentyl group, a cyclohexyl group, and the like are included.

In the above-mentioned "alkenyl group which may have substituent(s)", examples of the "alkenyl group" include an alkenyl group having 2 to 18 carbon atoms. An alkenyl group having 2 to 10 carbon atoms is even more preferred. Specifically, a vinyl group, a propenyl group, a 3-butenyl group, and the like are included.

In the above-mentioned "cycloalkenyl group which may have substituent(s)", examples of the "cycloalkenyl group" include a cycloalkenyl group having 5 to 18 carbon atoms. A cycloalkenyl group having 5 to 10 carbon atoms is even more preferred. Specifically, a cyclohexenyl group, a cyclooctenyl group, a cyclododecenyl group, and the like are included.

In the above-mentioned "aryl group which may have substituent(s)", examples of the "aryl group" include an aryl group having 6 to 14 carbon atoms. An aryl group having 6 to 10 carbon atoms is even more preferred. Specifically, a phenyl group, a tolyl group, a naphtyl group, and the like are included.

In the above-mentioned "arylalkyl group which may have substituent(s)", examples of the "arylalkyl group" include an arylalkyl group having 7 to 13 carbon atoms. An arylalkyl group having 7 to 9 carbon atoms is even more preferred. Specifically, a benzyl group, a phenethyl group, a naphtylmethyl group, a naphtylethyl group, and the like are included.

An aryl group which may have substituent(s) is preferably used as the hydrocarbon group. Specifically, diphenyl carbonate, bis(4-nitrophenyl) carbonate, bis(2-nitrophenyl) carbonate, bis(2,4-dinitrophenyl) carbonate, bis(2,4,6-trinitrophenyl) carbonate, bis(pentafluorophenyl) carbonate, bis(4-chlorophenyl) carbonate, bis(2,4-dichlorophenyl) carbonate, bis(2,4,6-trichlorophenyl) carbonate, and the like are included. Of those, diphenyl carbonate is even more preferably used.

It should be noted that the carbonic acid diesters described above each can be produced by a known method and commercially available products of the diesters can be used.

Hereinafter, the method for production of an N-carboxy amino acid anhydride is described.

(1) Step of Production of Amino Acid Carbamate

In the method for production of an amino acid carbamate of the present invention, the carbonic acid diester represented by the formula (2) is used in an amount of preferably 1 to 10 mol, more preferably 1 to 3 mol, with respect to 1 mol of the amino acid organic salt compound represented by the formula (1).

In addition, a reaction temperature in the method for production of an amino acid carbamate of the present invention is preferably −30° C. to 35° C., more preferably −20° C. to 25° C. In addition, a reaction time is preferably 0.01 to 15 hours, more preferably 0.1 to 8 hours.

In addition, the method for production of an amino acid carbamate of the present invention can be performed in the presence or absence of a catalyst, and is typically performed in the presence of a solvent.

Examples of the solvent include: amide-based solvents such as dimethylacetamide, dimethylformamide, and N-methylpyrrolidone; sulfoxide-based solvents such as dimethylsulfoxide; ketone-based solvents such as 2-butanone, methyl ethyl ketone, and acetone; ester-based solvents such as ethyl acetate and butyl acetate; nitrile-based solvents such as acetonitrile; halogen-based solvents such as chloroform and dichloromethane; ether-based solvents such as tetrahydrofuran and cyclopentane monomethyl ether; and alcohol-based solvents such as methanol, ethanol, and butanol. Of those, 2-butanone, acetonitrile, dichloromethane, chloroform, methanol, and ethanol are preferred, 2-butanone, acetonitrile, and dichloromethane are more preferred, and 2-butanone and acetonitrile are still more preferred.

The solvent is used in an amount of typically 100 to 3,000 parts by weight, preferably 1,000 to 2,000 parts by weight with respect to 100 parts by weight of the total amount of the amino acid organic salt compound and the carbonic acid diester.

It should be noted that the production of the amino acid carbamate can be performed in one pot with the production of the amino acid organic salt compound represented by the formula (1).

(2) Step of Production of N-Carboxy Amino Acid Anhydride

Subsequently, an N-carboxyamino acid anhydride can be obtained by the step of cyclizing the resultant amino acid carbamate.

Although the step of cyclizing the resultant amino acid carbamate is not particularly limited, the reaction is preferably performed in the presence of a weak basic inorganic compound or a protonic acid from such a viewpoint that the N-carboxy amino acid anhydride is obtained in high yield.

Examples of the weak basic inorganic compound to be used include solid basic compounds such as a crystalline aluminosilicate, sodium hydrogen carbonate, alumina, zeolites, an ion exchange resin, and silica gel. Specific examples of the weak basic inorganic compound include molecular sieves and sodium hydrogen carbonate. The weak basic inorganic compound is used in an amount of preferably 1 to 1,000 parts by weight, even more preferably 1 to 10 parts by weight with respect to 100 parts by weight of the amino acid carbamates (1).

In addition, examples of the protonic acid to be used include phenols, phosphoric acids, sulfonic acids, and compounds each represented by a general formula (40).

$$R^{35}(C(R^{36})(R^{37}))_n COOH \quad (40)$$

(In the formula, $R^{35}$, $R^{36}$, and $R^{37}$ each independently represent a hydrogen atom, an alkyl group which may have substituent(s), an aryl group which may have substituent(s), a halogen atom, a hydroxyl group, an alkoxy group, an aryloxy group, a ketone group, an ester group, or a carboxyl group, and n represents a number of 0 to 10, provided that, in the case of n=0, $R^{35}$ represents a hydrogen atom, an alkyl group which may have substituent(s), or an aryl group which may have substituent(s).)

Of those, the phenols and the compounds each represented by the above-mentioned general formula (40) are preferred. Examples of the phenols include phenols substituted with electron-withdrawing groups, such as 2,4-dinitrophenol, pentafluorophenol, cyanophenol, and (2-butanone)phenol.

In the general formula (40), examples of the alkyl group represented by any one of $R^{35}$, $R^{36}$, and $R^{37}$ include a linear or branched alkyl group having 1 to 12 carbon atoms. Examples of the aryl group include an aryl group having 6 to 14 carbon atoms. A phenyl group, a naphthyl group, and the like are preferred. Examples of the halogen atom include fluorine, chlorine, bromine, and iodine. Examples of the alkoxy group include a linear or branched alkoxy group having 1 to 12 carbon atoms. Examples of the aryloxy group include an aryloxy group having 6 to 14 carbon atoms. A phenoxy group and the like are preferred. Examples of a group which can substitute the alkyl group or the aryl group include 1 to 5 groups selected from a halogen atom, a nitro group, a hydroxy group, a mercapto group, a cyano group, an alkoxy group, and the like.

It is preferred that, in a compound represented by the general formula (40), $R^{35}$, $R^{36}$, and $R^{37}$ be each independently selected from a hydrogen atom and an aryl group which may have substituent(s), and n represent 0 or 1. Further, in the case of n=0, $R^{35}$ even more preferably represents a phenyl group which may have substituent(s). It is even more preferred that, in the case of n=1, $R^{35}$, $R^{36}$, and $R^{37}$ each independently represent a hydrogen atom or a phenyl group which may have substituent(s). Specifically, benzoic acid, p-nitrobenzoic acid, pentafluorobenzoic acid, 2,4-dinitrobenzoic acid, phenylacetic acid, diphenylacetic acid, or the like is suitably used.

Examples of the phosphoric acids include phosphoric acid, phosphorous acid, and hypophosphorous acid.

Examples of the sulfonic acids include an aliphatic sulfonic acid, an aromatic sulfonic acid, and a sulfuric acid. Specifically, there are preferably used a methanesulfonic acid, an ethanesulfonic acid, a p-toluenesulfonic acid, and a benzenesulfonic acid.

The protonic acid is used in an amount of preferably 0.1 to 10 mol, even more preferably 0.5 to 10 mol with respect to 1 mol of the amino acid carbamates (1).

In the reaction, the weak basic inorganic compound may serve as a catalyst and the protonic acid may suppress the decomposition of the N-carboxy amino acid anhydride.

The reaction is preferably performed in an organic solvent. Specific examples of the organic solvents which can be used in the present invention include: ethers such as tetrahydrofuran, 1,4-dioxane, diethyl ether, and ethylene glycol dimethyl ether; halogenated aliphatic hydrocarbons such as chloroform and dichloromethane; esters such as ethyl acetate and butyl acetate; ketones such as acetone, methyl ethyl ketone, and methyl isobutyl ketone; aromatic hydrocarbons such as benzene, toluene, and xylene; nitriles such as acetonitrile and propionitrile; carbonates such as dimethyl carbonate; aliphatic hydrocarbons such as hexane and petroleum ether; and halogenated aromatic hydrocarbons such as chlorobenzene and dichlorobenzene. The use of the organic solvent is not compulsory, and the amount in which the organic solvent is used is not particularly limited. In addition, one kind of those solvents may be used alone, or two or more kinds of them may be used as a mixture.

A condition for the reaction in the step of cyclizing the amino acid carbamate is not particularly limited. The reaction, which can be typically performed in the air, is desirably performed under an inert gas atmosphere such as argon or nitrogen because a compound to be used and the product decompose owing to moisture. It should be noted that the reaction can be performed under any one of normal pressure, reduced pressure, and increased pressure. A reaction temperature is desirably selected from the range of typically −70° C. to 120° C., preferably −10° C. to 100° C. A required reaction time is typically 0.1 to 100 hours.

The target compound can be separated from a reaction system through isolation and purification by appropriately combining typical means such as filtration, washing, drying, recrystallization, centrifugal separation, an activated carbon treatment, extraction with various solvents, and chromatography.

EXAMPLES

Example 1

Under a nitrogen atmosphere, 428 mg (2 mmol) of diphenyl carbonate and 5 mL of acetonitrile were loaded into a round bottom flask having a volume of 100 mL, and then the mixture was stirred at room temperature. A solution prepared by dissolving 514 mg (2 mmol) of 1-ethyl-3-methylimidazolium glutamate in 15 mL of acetonitrile was slowly dropped to the solution, and then the mixture was stirred for 30 minutes. After that, a 1M aqueous HCl solution was added to the reaction solution to terminate the reaction, and then the resultant was concentrated with an evaporator. Next, water was added to the concentrated product, and then the resultant was extracted with ethyl acetate. The resultant organic layer was washed with water and brine, and was then dried with sodium sulfate.

After that, the dried product was concentrated with an evaporator. Thus, a crude product was obtained. Next, the crude product was purified by column chromatography. Thus, N-phenoxycarbonyl-L-glutamic acid was obtained. An isolation amount and an isolation yield were 421.8 mg and 79%, respectively.

Subsequently, under a nitrogen atmosphere, 267 mg (1 mmol) of N-phenoxycarbonyl-L-glutamic acid, 8 mg (2 wt %) of molecular sieve 4A, 122 mg (1.0 mmol) of benzoic acid, and 10 mL of 2-butanone were loaded into a two-necked round bottom flask having a volume of 100 mL and mounted with a Dimroth condenser, and then the mixture was stirred at 80° C. for 29 hours. The fact that N-carboxy-α-glutamic acid anhydride was obtained in a yield of 89% was confirmed by subjecting the reaction mixture to NMR determination with dioxane as an internal standard.

Example 2

Under a nitrogen atmosphere, 428 mg (2 mmol) of diphenyl carbonate and 5 mL of 2-butanone were loaded into a round bottom flask having a volume of 100 mL, and then the mixture was stirred at room temperature. A solution prepared by dissolving 550 mg (2 mmol) of 1-ethyl-3-methylimidazolium phenylalanine salt in 15 mL of 2-butanone was slowly dropped to the solution, and then the mixture was stirred for 2 hours.

The production of N-phenoxycarbonyl-L-phenylalanine was confirmed by NMR measurement.

Subsequently, under a nitrogen atmosphere, 571 mg (2 mmol) of N-phenoxycarbonyl-L-phenylalanine, 212 mg (1 mmol) of diphenylacetic acid, and 20 mL of 2-butanone were loaded into a two-necked round bottom flask having a volume of 100 mL and mounted with a Dimroth condenser, and then the mixture was stirred at 80° C. for 30 hours. The fact that N-carboxy-phenylalanine anhydride was obtained in a yield of 99% or more was confirmed by subjecting the reaction mixture to NMR determination.

Example 3

Under a nitrogen atmosphere, 430 mg (2 mmol) of diphenyl carbonate and 5 mL of 2-butanone were loaded into a round bottom flask having a volume of 100 mL, and then the mixture was stirred at −20° C. A solution prepared by dissolving 550 mg (2 mmol) of 1-ethyl-3-methylimidazolium phenylalanine salt in 15 mL of 2-butanone was slowly dropped to the solution, and then the mixture was stirred at −20° C. for 8 hours. After that, a 1M aqueous HCl solution was added to the mixture to terminate the reaction. The resultant was concentrated with an evaporator. Next, water was added to the concentrated product, and then the resultant was extracted with ethyl acetate. After that, the resultant was concentrated with an evaporator. Thus, a crude product was obtained. Next, the crude product was purified by column chromatography. Thus, N-phenoxycarbonyl-L-phenylalanine was obtained. An isolation amount and an isolation yield were 528.9 mg and 93%, respectively.

Under a nitrogen atmosphere, 571 mg (2 mmol) of N-phenoxycarbonyl-L-phenylalanine, 424 mg (2 mmol) of diphenylacetic acid, and 20 mL of acetonitrile were loaded into a two-necked round bottom flask having a volume of 100 mL and mounted with a Dimroth condenser, and then the mixture was stirred at 80° C. for 30 hours. The fact that N-carboxy-phenylalanine anhydride was obtained in a yield of 99% or more was confirmed by subjecting the reaction mixture to NMR determination.

Example 4

Under a nitrogen atmosphere, 428 mg (2 mmol) of diphenyl carbonate and 5 mL of acetonitrile were loaded into a round bottom flask having a volume of 100 mL, and then the mixture was stirred at room temperature. A solution prepared by dissolving 552 mg (2 mmol) of 1-ethyl-3-methylimidazolium phenylalanine salt in 15 mL of acetonitrile was slowly dropped to the solution, and then the mixture was stirred for 5 minutes. After that, a 1M aqueous HCl solution was added to the reaction solution to terminate the reaction, and then the resultant was concentrated with an evaporator. Next, water was added to the concentrated product, and then the resultant was extracted with ethyl acetate. The resultant organic layer was washed with water and brine, and was then dried with sodium sulfate.

After that, the dried product was concentrated with an evaporator. Thus, a crude product was obtained. Next, the crude product was purified by column chromatography. Thus, N-phenoxycarbonyl-L-phenylalanine was obtained. An isolation amount and an isolation yield were 506.0 mg and 88%, respectively.

Under a nitrogen atmosphere, 571 mg (2 mmol) of N-phenoxycarbonyl-L-phenylalanine, 360 mg (6 mmol) of acetic acid, and 20 mL of acetonitrile were loaded into a two-necked round bottom flask having a volume of 100 mL and mounted with a Dimroth condenser, and then the mixture was stirred at 80° C. for 29 hours. The fact that N-carboxy-phenylalanine anhydride was obtained in a yield of 99% or more was confirmed by subjecting the reaction mixture to NMR determination. After the reaction mixture had been cooled to room temperature, 2 mL of a 1M aqueous solution of hydrochloric acid and 2,400 mg of activated carbon were added to the resultant, and then the mixture was stirred for 1 hour. The activated carbon was removed by filtration, and then the resultant filtrate was concentrated under reduced pressure. Thus, N-carboxy-phenylalanine anhydride was obtained. An isolation amount and an isolation yield were 302.5 mg and 78%, respectively.

Example 5

Under a nitrogen atmosphere, 430 mg (2 mmol) of diphenyl carbonate and 5 mL of dichloromethane were loaded into a round bottom flask having a volume of 100 mL, and then the mixture was stirred at room temperature. A solution prepared by dissolving 549 mg (2 mmol) of 1-ethyl-3-methylimidazolium phenylalanine salt in 15 mL of dichloromethane was slowly dropped to the solution, and then the mixture was stirred for 30 minutes. After that, a 1M aqueous HCl solution was added to the reaction solution to terminate the reaction, and then the resultant was concentrated with an evaporator. Next, water was added to the concentrated product, and then the resultant was extracted with ethyl acetate. The resultant organic layer was washed with water and brine, and was then dried with sodium sulfate.

After that, the dried product was concentrated with an evaporator. Next, the concentrated product was purified by column chromatography. Thus, N-phenoxycarbonyl-L-phenylalanine was obtained. An isolation amount and an isolation yield were 390.2 mg and 68%, respectively.

Under a nitrogen atmosphere, a solution prepared by dissolving 571 mg (2 mmol) of N-phenoxycarbonyl-L-phenylalanine, 424 mg (2 mmol) of diphenylacetic acid, and 94 mg (1 mmol) of phenol in 20 mL of 2-butanone was charged into a two-necked round bottom flask having a volume of 100 mL and mounted with a Dimroth condenser, and was then stirred at 80° C. for 15 hours. The fact that N-carboxy-phenylalanine anhydride was obtained in a yield of 99% or more was confirmed by subjecting the reaction mixture to NMR determination.

Example 6

Under a nitrogen atmosphere, 430 mg (2 mmol) of diphenyl carbonate and 5 mL of 2-butanone were loaded into a round bottom flask having a volume of 100 mL, and then the mixture was stirred at 0° C. A solution prepared by dissolving 550 mg (2 mmol) of 1-ethyl-3-methylimidazolium phenylalanine salt in 15 mL of 2-butanone was slowly dropped to the solution, and then the mixture was stirred at 0° C. for 2 hours. After that, a 1M aqueous HCl solution was added to the mixture to terminate the reaction. The resultant was concentrated with an evaporator. Next, water was added to the concentrated product, and then the resultant was extracted with ethyl acetate. The resultant two organic layers were washed with water and brine, and were then dried with sodium sulfate.

After that, the dried product was concentrated with an evaporator. Thus, a crude product was obtained. Next, the crude product was purified by column chromatography. Thus, N-phenoxycarbonyl-L-phenylalanine was obtained. An isolation amount and an isolation yield were 384.6 mg and 67%, respectively.

Under a nitrogen atmosphere, a solution prepared by dissolving 571 mg (2 mmol) of N-phenoxycarbonyl-L-phenylalanine, 424 mg (2 mmol) of diphenylacetic acid, and 184 mg (2 mmol) of phenol in 20 mL of 2-butanone was charged into a two-necked round bottom flask having a volume of 100 mL and mounted with a Dimroth condenser, and was then stirred at 80° C. for 12 hours. The fact that N-carboxy-phenylalanine anhydride was obtained in a yield of 99% or more was confirmed by subjecting the reaction mixture to NMR determination.

Example 7

Under a nitrogen atmosphere, 428 mg (2 mmol) of diphenyl carbonate and 5 mL of acetonitrile were loaded into a round bottom flask having a volume of 100 mL, and then the mixture was stirred at room temperature. A solution prepared by dissolving 396 mg (2 mmol) of 1-ethyl-3-methylimidazolium alanine salt in 15 mL of acetonitrile was slowly dropped to the solution, and then the mixture was stirred for 20 minutes. After that, a 1M aqueous HCl solution was added to the reaction solution to terminate the reaction, and then the resultant was concentrated with an evaporator. Next, water was added to the concentrated product, and then the resultant was extracted with ethyl acetate. The resultant organic layer was washed with water and brine, and was then dried with sodium sulfate.

After that, the dried product was concentrated with an evaporator. Thus, a crude product was obtained. Next, the crude product was purified by column chromatography. Thus, N-phenoxycarbonyl-alanine was obtained. An isolation amount and an isolation yield were 337.5 mg and 81%, respectively.

Example 8

Under a nitrogen atmosphere, 428 mg (2 mmol) of diphenyl carbonate and 5 mL of acetonitrile were loaded into a round bottom flask having a volume of 100 mL, and then the mixture was stirred at room temperature. A solution prepared by dissolving 627 mg (2 mmol) of 1-ethyl-3-methylimidazolium-γ-t-butyl-L-glutamate in 15 mL of acetonitrile was slowly dropped to the solution, and then the mixture was stirred for 10 minutes. After that, a 1M aqueous HCl solution was added to the reaction solution to terminate the reaction, and then the resultant was concentrated with an evaporator. Next, water was added to the concentrated product, and then the resultant was extracted with ethyl acetate. The resultant organic layer was washed with water and brine, and was then dried with sodium sulfate.

After that, the dried product was concentrated with an evaporator. Thus, a crude product was obtained. Next, the crude product was purified by column chromatography. Thus, N-phenoxycarbonyl-γ-t-butyl-L-glutamate was obtained. An isolation amount and an isolation yield were 470.1 mg and 76%, respectively.

Example 9

Under a nitrogen atmosphere, 0.330 g (2 mmol) of phenylalanine, 0.250 g of molecular sieve 4A, and 5 mL of 2-butanone were loaded into a round bottom flask having a volume of 100 mL, and then the mixture was stirred at room temperature. Next, 1.044 mL of a 38.7% solution of tetrabutylammonium hydroxide in methanol (Tokyo Chemical Industry Co., Ltd.) was slowly dropped to the solution, and then the mixture was stirred for 30 minutes. After that, 430 mg (2 mmol) of diphenyl carbonate were added to the mixture, and then the whole was stirred for 20 hours. The molecular sieve 4A was removed by filtration of the reaction solution. A 1M aqueous HCl solution was added to the resultant filtrate to terminate the reaction, and then the resultant was concentrated with an evaporator. Next, water was added to the concentrated product, and then the resultant was extracted with ethyl acetate. The resultant organic layer was washed with water and brine, and was then dried with sodium sulfate. After that, the dried product was concentrated with an evaporator. Thus, a crude product was obtained. Next, the crude product was purified by column chromatography. Thus, the production of N-phenoxycarbonyl-L-alanine was confirmed. An isolation amount and an isolation yield were 294.4 mg and 51%, respectively.

Under a nitrogen atmosphere, a solution prepared by dissolving 571 mg (2 mmol) of N-phenoxycarbonyl-L-phenylalanine, 424 mg (2 mmol) of diphenylacetic acid, and 376 mg (4 mmol) of phenol in 20 mL of 2-butanone was charged into a two-necked round bottom flask having a volume of 100 mL and mounted with a Dimroth condenser, and was then stirred at 80° C. for 18 hours. The fact that N-carboxy-phenylalanine anhydride was obtained in a yield of 99% or more was confirmed by subjecting the reaction mixture to NMR determination.

Example 10

Under a nitrogen atmosphere, 0.294 g (2 mmol) of glutamic acid, 0.250 g of molecular sieve 4A, and 5 mL of 2-butanone were loaded into a round bottom flask having a volume of 100 mL, and then the mixture was stirred at room temperature. Next, 1.044 mL of a 38.7% solution of tetrabutylammonium hydroxide in methanol (Tokyo Chemical Industry Co., Ltd.) was slowly dropped to the solution, and then the mixture was stirred for 30 minutes. After that, 430 mg (2 mmol) of diphenyl carbonate were added to the mixture, and then the whole was stirred for 20 hours. The molecular sieve 4A was removed by filtration of the reaction solution. A 1M aqueous HCl solution was added to the resultant filtrate to terminate the reaction, and then the resultant was concentrated with an evaporator. Next, water was added to the concentrated product, and then the resultant was extracted with ethyl acetate. The resultant organic layer was washed with water and brine, and was then dried with sodium sulfate. After that, the dried product was concentrated with an evaporator. Thus, a crude product was obtained. Next, the crude product was purified by column chromatography. Thus, the production of N-phenoxycarbonyl-L-glutamic acid was confirmed. An isolation amount and an isolation yield were 294.4 mg and 51%, respectively.

Example 11

Under a nitrogen atmosphere, 428 mg (2 mmol) of diphenyl carbonate and 5 mL of acetonitrile were loaded into a round bottom flask having a volume of 100 mL, and then the mixture was stirred at room temperature. Next, 482 mg (2 mmol) of 1-ethyl-3-methylimidazolium leucine salt and 15 mL of acetonitrile were slowly dropped to the solution, and then the mixture was stirred for 30 minutes. After that, a 1M aqueous HCl solution was added to the reaction solution to terminate the reaction, and then the resultant was concentrated with an evaporator. Next, water was added to the concentrated product, and then the resultant was extracted with ethyl acetate. The resultant organic layer was washed with water and brine, and was then dried with sodium sulfate.

After that, the dried product was concentrated with an evaporator. Thus, a crude product was obtained. Next, the crude product was purified by column chromatography. Thus, N-phenoxycarbonyl-L-leucine was obtained. An isolation amount and an isolation yield were 399.5 mg and 80%, respectively.

Example 12

Under a nitrogen atmosphere, 428 mg (2 mmol) of diphenyl carbonate and 5 mL of acetonitrile were loaded into a round bottom flask having a volume of 100 mL, and then the mixture was stirred at room temperature. Next, 519 mg (2 mmol) of 1-ethyl-3-methylimidazolium methionine salt and 15 mL of acetonitrile were slowly dropped to the solution, and then the mixture was stirred for 20 minutes. After that, a 1M aqueous HCl solution was added to the reaction solution to terminate the reaction, and then the resultant was concentrated with an evaporator. Next, water was added to the concentrated product, and then the resultant was extracted with ethyl acetate. The resultant organic layer was washed with water and brine, and was then dried with sodium sulfate.

After that, the dried product was concentrated with an evaporator. Thus, a crude product was obtained. Next, the crude product was purified by column chromatography. Thus, N-phenoxycarbonyl-L-methionine was obtained. An isolation amount and an isolation yield were 439.2 mg and 820, respectively.

Example 13

Under a nitrogen atmosphere, 428 mg (2 mmol) of diphenyl carbonate and 5 mL of acetonitrile were loaded into a round bottom flask having a volume of 100 mL, and then the mixture was stirred at room temperature. Next, 847 mg (2 mmol) of tetrabutylphosphonium phenylalanine salt and 15 mL of acetonitrile were slowly dropped to the solution, and then the mixture was stirred for 30 minutes. After that, a 1M aqueous HCl solution was added to the reaction solution to terminate the reaction, and then the resultant was concentrated with an evaporator. Next, water was added to the concentrated product, and then the resultant was extracted with ethyl acetate. The resultant organic layer was washed with water and brine, and was then dried with sodium sulfate.

After that, the dried product was concentrated with an evaporator. Thus, a crude product was obtained. Next, the crude product was purified by column chromatography. Thus, N-phenoxycarbonyl-L-phenylalanine was obtained. An isolation amount and an isolation yield were 417.0 mg and 73%, respectively.

Under a nitrogen atmosphere, a solution prepared by dissolving 571 mg (2 mmol) of N-phenoxycarbonyl-L-phenylalanine and 184 mg (2 mmol) of phenol in 20 mL of 2-butanone was charged into a two-necked round bottom flask having a volume of 100 mL and mounted with a Dimroth condenser, and was then stirred at 80° C. for 8 hours. The fact that N-carboxy-phenylalanine anhydride was obtained in a yield of 99% or more was confirmed by subjecting the reaction mixture to NMR determination.

Example 14

Under a nitrogen atmosphere, 428 mg (2 mmol) of diphenyl carbonate and 5 mL of acetonitrile were loaded into a round bottom flask having a volume of 100 mL, and then the mixture was stirred at room temperature. Next, 813 mg (2 mmol) of tetrabutylammonium phenylalanine salt and 15 mL of acetonitrile were dropped to the solution, and then the mixture was stirred for 15 minutes. After that, a 1M aqueous HCl solution was added to the reaction solution to terminate the reaction, and then the resultant was concentrated with an evaporator. Next, water was added to the concentrated product, and then the resultant was extracted with ethyl acetate. The resultant organic layer was washed with water and brine, and was then dried with sodium sulfate. After that, the dried product was concentrated with an evaporator. Thus, a crude product was obtained. Next, the crude product was purified by column chromatography. Thus, N-phenoxycarbonyl-L-alanine was obtained. An isolation amount and an isolation yield were 445.0 mg and 78%, respectively.

Example 15

Under a nitrogen atmosphere, 428 mg (2 mmol) of diphenyl carbonate and 5 mL of acetonitrile were loaded into a round bottom flask having a volume of 100 mL, and then the mixture was stirred at room temperature. Next, 633 mg (2 mmol) of tetrabutylammonium phenylglycine salt and 15 mL of acetonitrile were dropped to the solution, and then the mixture was stirred for 20 minutes. After that, a 1M aqueous HCl solution was added to the reaction solution to terminate the reaction, and then the resultant was concentrated with an evaporator. Next, water was added to the concentrated product, and then the resultant was extracted with ethyl acetate. The resultant organic layer was washed with water and brine, and was then dried with sodium sulfate. After that, the dried product was concentrated with an evaporator. Thus, a crude product was obtained. Next, the crude product was purified by column chromatography. Thus, N-phenoxycarbonyl-L-glycine was obtained. An isolation amount and an isolation yield were 328.2 mg and 84%, respectively.

Example 16

Under a nitrogen atmosphere, 428 mg (2 mmol) of diphenyl carbonate and 5 mL of acetonitrile were loaded into a round bottom flask having a volume of 100 mL, and then the mixture was stirred at room temperature. Next, 847 mg (2 mmol) of tetrabutylphosphonium phenylalanine salt and 15 mL of acetonitrile were dropped to the solution, and then the mixture was stirred for 15 minutes. After that, a 1M aqueous HCl solution was added to the reaction solution to terminate the reaction, and then the resultant was concentrated with an evaporator. Next, water was added to the concentrated product, and then the resultant was extracted with ethyl acetate. The resultant organic layer was washed with water and brine, and was then dried with sodium sulfate. After that, the dried product was concentrated with an evaporator. Thus, a crude product was obtained. Next, the crude product was purified by column chromatography. Thus, N-phenoxycarbonyl-L-alanine was obtained. An isolation amount and an isolation yield were 416.6 mg and 73%, respectively.

Example 17

Under a nitrogen atmosphere, 428 mg (2 mmol) of diphenyl carbonate and 5 mL of acetonitrile were loaded into a round bottom flask having a volume of 100 mL, and then the mixture was stirred at room temperature. Next, 966 mg (2 mmol) of butyl-triphenylphosphonium phenylalanine salt and 15 mL of acetonitrile were dropped to the solution, and then the mixture was stirred for 20 minutes. After that, a 1M aqueous HCl solution was added to the reaction solution to terminate the reaction, and then the resultant was concentrated with an evaporator. Next, water was added to the concentrated product, and then the resultant was extracted with ethyl acetate. The resultant organic layer was washed with water and brine, and was then dried with sodium sulfate. After that, the dried product was concentrated with an evaporator. Thus, a crude product was obtained. Next, the crude product was purified by column chromatography. Thus, N-phenoxycarbonyl-L-alanine was obtained. An isolation amount and an isolation yield were 496.3 mg and 87%, respectively.

Example 18

Under a nitrogen atmosphere, 428 mg (2 mmol) of diphenyl carbonate and 5 mL of acetonitrile were loaded into a round bottom flask having a volume of 100 mL, and then the mixture was stirred at room temperature. Next, 618 mg (2 mmol) of S-benzyltetrahydrothiophenium phenylalanine salt and 15 mL of acetonitrile were dropped to the solution, and then the mixture was stirred for 30 minutes. After that, a 1M aqueous HCl solution was added to the reaction solution to terminate the reaction, and then the resultant was concentrated with an evaporator. Next, water was added to the concentrated product, and then the resultant was extracted with ethyl acetate. The resultant organic layer was washed with water and brine, and was then dried with sodium sulfate. After that, the dried product was concentrated with an evaporator. Thus, a crude product was obtained. Next, the crude product was purified by column chromatography. Thus, N-phenoxycarbonyl-L-alanine was obtained. An isolation amount and an isolation yield were 456.2 mg and 80%, respectively.

Example 19

Under a nitrogen atmosphere, 0.330 g (2 mmol) of phenylalanine, 0.99 g of molecular sieve 4A, and 10 mL of acetonitrile were loaded into a round bottom flask having a volume of 100 mL, and then the mixture was stirred at room temperature. A solution of 0.518 g of tetrabutylammonium hydroxide in 10 mL of acetonitrile was dropped to the solution, and then the mixture was stirred for 30 minutes. After that, 430 mg (2 mmol) of diphenyl carbonate were added to the mixture, and then the whole was stirred for 3 hours. The molecular sieve 4A was removed by filtration of the reaction solution. A 1M aqueous HCl solution was added to the resultant filtrate to terminate the reaction, and then the resultant was concentrated with an evaporator. Next, water was added to the concentrated product, and then the resultant was extracted with ethyl acetate. The resultant organic layer was washed with water and brine, and was then dried with sodium sulfate. After that, the dried product was concentrated with an evaporator. Thus, a crude product was obtained. Next, the crude product was purified by column chromatography. Thus, the production of N-phenoxycarbonyl-L-alanine was confirmed. An isolation amount and an isolation yield were 445.2 mg and 78%, respectively.

Example 20

Under a nitrogen atmosphere, 0.330 g (2 mmol) of phenylalanine, 1.60 g of molecular sieve 4A, and 10 mL of acetonitrile were loaded into a round bottom flask having a volume of 100 mL, and then the mixture was stirred at room temperature. A solution of 0.518 g of tetrabutylammonium hydroxide in 10 mL of acetonitrile was dropped to the solution, and then the mixture was stirred for 30 minutes. After that, 430 mg (2 mmol) of diphenyl carbonate were added to the mixture, and then the whole was stirred for 3 hours. The molecular sieve 4A was removed by filtration of the reaction solution. A 1M aqueous HCl solution was added to the resultant filtrate to terminate the reaction, and then the resultant was concentrated with an evaporator. Next, water was added to the concentrated product, and then the resultant was extracted with ethyl acetate. The resultant organic layer was washed with water and brine, and was then dried with sodium sulfate. After that, the dried product was concentrated with an evaporator. Thus, a crude product was obtained. Next, the crude product was purified by column chromatography. Thus, the production of N-phenoxycarbonyl-L-alanine was confirmed. An isolation amount and an isolation yield were 484.2 mg and 85%, respectively.

Example 21

Under a nitrogen atmosphere, 0.330 g (2 mmol) of phenylalanine, 0.426 g (3 mmol) of anhydrous sodium sulfate, and 10 mL of acetonitrile were loaded into a round bottom flask having a volume of 100 mL, and then the mixture was stirred at room temperature. A solution of 0.518 g of tetrabutylammonium hydroxide in 10 mL of acetonitrile was dropped to the solution, and then the mixture was stirred for 30 minutes. After that, 430 mg (2 mmol) of diphenyl carbonate were added to the mixture, and then the whole was stirred for 3 hours. Anhydrous sodium sulfate was removed by filtrating the reaction solution. A 1M aqueous HCl solution was added to the resultant filtrate to terminate the reaction, and then the resultant was concentrated with an evaporator. Next, water was added to the concentrated product, and then the resultant was extracted with ethyl acetate. The resultant organic layer was washed with water and brine, and was then dried with sodium sulfate. After that, the dried product was concentrated with an evaporator. Thus, a crude product was obtained. Next, the crude product was purified by column chromatography. Thus, the production of N-phenoxycarbonyl-L-alanine was confirmed. An isolation amount and an isolation yield were 399 mg and 70%, respectively.

Example 22

Under a nitrogen atmosphere, 0.330 g (2 mmol) of phenylalanine, 1.42 g (10 mmol) of anhydrous sodium sulfate, and 10 mL of acetonitrile were loaded into a round bottom flask having a volume of 100 mL, and then the mixture was stirred at room temperature. A solution of 0.518 g of tetrabutylammonium hydroxide in 10 mL of acetonitrile was dropped to the solution, and then the mixture was stirred for 30 minutes. After that, 430 mg (2 mmol) of diphenyl carbonate were added to the mixture, and then the whole was stirred for 2 hours. Anhydrous sodium sulfate was removed by filtration of the reaction solution. A 1M aqueous HCl solution was added to the resultant filtrate to terminate the reaction, and then the resultant was concentrated with an evaporator. Next, water was added to the concentrated product, and then the resultant was extracted with ethyl acetate. The resultant organic layer was washed with water and brine, and was then dried with sodium sulfate. After that, the dried product was concentrated with an evaporator. Thus, a crude product was obtained. Next, the crude product was purified by column chromatography. Thus, the production of N-phenoxycarbonyl-L-alanine was confirmed. An isolation amount and an isolation yield were 490 mg and 86%, respectively.

Example 23

Under a nitrogen atmosphere, 428 mg (2 mmol) of diphenyl carbonate and 5 mL of acetonitrile were loaded into a round bottom flask having a volume of 100 mL, and then the mixture was stirred at room temperature. Next, 743 mg (2 mmol) of tetrabutylammonium 6-amino-n-caproate and 15 mL of acetonitrile were dropped to the solution, and then the mixture was stirred for 30 hours. The fact that N-phenoxycarbonyl-6-amino-n-caproic acid was produced in a yield of 85% was confirmed by NMR measurement.

Example 24

Under a nitrogen atmosphere, 428 mg (2 mmol) of diphenyl carbonate and 5 mL of acetonitrile were loaded into a round bottom flask having a volume of 100 mL, and then the mixture was stirred at room temperature. A solution prepared by dissolving 814 mg (2 mmol) of tetrabutylphosphonium methionine salt in 15 mL of acetonitrile was dropped to the solution, and then the mixture was stirred for 30 minutes. After that, a 1M aqueous HCl solution was added to the reaction solution to terminate the reaction, and then the resultant was concentrated with an evaporator. Next, water was added to the concentrated product, and then the resultant was extracted with ethyl acetate. The resultant organic layer was washed with water and brine, and was then dried with sodium sulfate. After that, the dried product was concentrated with an evaporator. Thus, a crude product was obtained. Next, the crude product was purified by column chromatography. Thus, N-phenoxycarbonyl-L-methionine was obtained. An isolation amount and an isolation yield were 430.9 mg and 80%, respectively.

Example 25

Under a nitrogen atmosphere, 428 mg (2 mmol) of diphenyl carbonate and 5 mL of acetonitrile were loaded into a round bottom flask having a volume of 100 mL, and then the mixture was stirred at room temperature. A solution prepared by dissolving 935 mg (2 mmol) of butyltriphenylphosphonium methionine salt in 15 mL of acetonitrile was dropped to the solution, and then the mixture was stirred for 50 minutes. After that, a 1M aqueous HCl solution was added to the reaction solution to terminate the reaction, and then the resultant was concentrated with an evaporator. Next, water was added to the concentrated product, and then the resultant was extracted with ethyl acetate. The resultant organic layer was washed with water and brine, and was then dried with sodium sulfate. After that, the dried product was concentrated with an evaporator. Thus, a crude product was obtained. Next, the crude product was purified by column chromatography. Thus, N-phenoxycarbonyl-L-methionine was obtained. An isolation amount and an isolation yield were 441.5 mg and 82%, respectively.

Example 26

Under a nitrogen atmosphere, 428 mg (2 mmol) of diphenyl carbonate and 5 mL of acetonitrile were loaded into a round bottom flask having a volume of 100 mL, and then the mixture was stirred at room temperature. A solution prepared by dissolving 633 mg (mL) of butyltetrahydrothiophenium methionine salt in 15 mL of acetonitrile was dropped to the solution, and then the mixture was stirred for 20 minutes. After that, a 1M aqueous HCl solution was added to the reaction solution to terminate the reaction, and then the resultant was concentrated with an evaporator. Next, water was added to the concentrated product, and then the resultant was extracted with ethyl acetate. The resultant organic layer was washed with water and brine, and was then dried with sodium sulfate. After that, the dried product was concentrated with an evaporator. Thus, a crude product was obtained. Next, the crude product was purified by column chromatography. Thus, N-phenoxycarbonyl-L-methionine was obtained. An isolation amount and an isolation yield were 428.8 mg and 80%, respectively.

The invention claimed is:

1. A method for production of an N-carboxy amino acid anhydride, comprising reacting an amino acid organic salt compound with a carbonic acid diester,
wherein the amino acid organic salt compound is represented by formula (1):

wherein $AX^+$ represents an organic onium ion and Y represents an optionally substituted divalent hydrocarbon group, and
wherein the carbonic acid diester is a compound represented by formula (2):

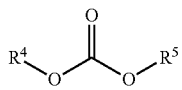

wherein $R^4$ and $R^5$ each independently represent an aryl group which may have substituent(s), wherein the substituent(s) are selected from the group consisting of a nitro group, halogen atoms, a perfluoroalkyl group, a perchloroalkyl group, an ester group, an acetyl group, a cyano group and a benzoyl group.

2. The method for production of an N-carboxy amino acid anhydride according to claim 1, wherein Y represents an optionally substituted divalent hydrocarbon group represented by formula (3):

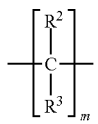

wherein $R^2$ and $R^3$ each independently represent a hydrogen atom or an optionally substituted monovalent hydrocarbon group, and m represents an integer of 1 to 15.

3. The method for production of an N-carboxy amino acid anhydride according to claim 1, wherein
X represents an atom selected from the group consisting of a nitrogen atom, a phosphorus atom, a sulfur atom, and an iodine atom; and
$AX^+$ represents an ion selected from the group consisting of an ammonium ion, a phosphonium ion, a sulfonium ion, and an iodonium ion.

4. The method for production of an N-carboxy amino acid anhydride according to claim 2, wherein
X represents an atom selected from the group consisting of a nitrogen atom, a phosphorus atom, a sulfur atom, and an iodine atom; and
$AX^+$ represents an ion selected from an ammonium ion, a phosphonium ion, a sulfonium ion, and an iodonium ion.

5. The method for production of an N-carboxy amino acid anhydride according to claim 2, wherein the amino acid anion in the formula (1) is an anion of an amino acid selected from the group consisting of L-leucine, L-phenylalanine, L-isoleucine, glycine, L-glutamic acid, L-valine, L-aspartic acid, L-tryptophan, L-alanine, L-arginine, L-asparagine, L-cysteine, L-glutamine, L-histidine, L-lysine, L-methionine, L-proline, L-serine, L-threonine, and L-tyrosine.

6. The method for production of an N-carboxy amino acid anhydride according to claim 2, wherein Y represents a divalent hydrocarbon group represented by formula (3), wherein $R^2$ and $R^3$ each independently represent a hydrogen atom or a monovalent hydrocarbon group, and m represents an integer of 1 to 15.

7. The method for production of an N-carboxy amino acid anhydride according to claim 1, wherein $R^4$ and $R^5$ each independently represent an unsubstituted aryl group.

8. The method for production of an N-carboxy amino acid anhydride according to claim 1, wherein $R^4$ and $R^5$ each independently represent a substituted aryl group.

9. The method for production of an N-carboxy amino acid anhydride according to claim 1, wherein $R^4$ and $R^5$ each independently represent an unsubstituted phenyl group.

10. The method for production of an N-carboxy amino acid anhydride according to claim 1, wherein $R^4$ and $R^5$ each independently represent a substituted phenyl group.

11. A method for production of an amino acid carbamate compound, comprising reacting an amino acid organic salt compound with a carbonic acid diester,
wherein the amino acid organic salt compound is represented by formula (1):

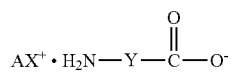

wherein $AX^+$ represents an organic onium ion and Y represents an optionally substituted divalent hydrocarbon group, and
wherein the carbonic acid diester is represented by formula (2):

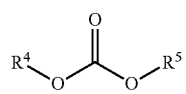

wherein $R^4$ and $R^5$ each independently represent an aryl group which may have substituent(s), wherein the substituent(s) are selected from the group consisting of a nitro group, halogen atoms, a perfluoroalkyl group, a perchloroalkyl group, an ester group, an acetyl group, a cyano group and a benzoyl group.

12. The method for production of an amino acid carbamate compound according to claim 11, wherein Y represents an optionally substituted divalent hydrocarbon group represented by formula (3):

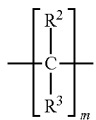

wherein $R^2$ and $R^3$ each independently represent a hydrogen atom or an optionally substituted monovalent hydrocarbon group, and m represents an integer of 1 to 15.

13. The method for production of an amino acid carbamate compound according to claim 11, wherein
X represents an atom selected from the group consisting of a nitrogen atom, a phosphorus atom, a sulfur atom, and an iodine atom; and
$AX^+$ represents an ion selected from the group consisting of an ammonium ion, a phosphonium ion, a sulfonium ion, and an iodonium ion.

14. The method for production of an amino acid carbamate compound according to claim 12, wherein
X represents an atom selected from the group consisting of a nitrogen atom, a phosphorus atom, a sulfur atom, and an iodine atom; and
$AX^+$ represents an ion selected from an ammonium ion, a phosphonium ion, a sulfonium ion, and an iodonium ion.

15. The method for production of an amino acid carbamate compound according to claim 11, wherein the amino acid anion in the formula (1) is an anion of an amino acid selected from the group consisting of L-leucine, L-phenylalanine, L-isoleucine, glycine, L-glutamic acid, L-valine, L-aspartic acid, L-tryptophan, L-alanine, L-arginine, L-asparagine, L-cysteine, L-glutamine, L-histidine, L-lysine, L-methionine, L-proline, L-serine, L-threonine, and L-tyrosine.

16. The method for production of an amino acid carbamate compound according to claim 12, wherein Y represents a divalent hydrocarbon group represented by formula (3), wherein $R^2$ and $R^3$ each independently represent a hydrogen atom or a monovalent hydrocarbon group, and m represents an integer of 1 to 15.

17. The method for production of an amino acid carbamate compound according to claim 11, wherein $R^4$ and $R^5$ each independently represent an unsubstituted aryl group.

18. The method for production of an amino acid carbamate compound according to claim 11, wherein $R^4$ and $R^5$ each independently represent a substituted aryl group.

19. The method for production of an amino acid carbamate compound according to claim 11, wherein $R^4$ and $R^5$ each independently represent an unsubstituted phenyl group.

20. The method for production of an amino acid carbamate compound according to claim 11, wherein $R^4$ and $R^5$ each independently represent a substituted phenyl group.

* * * * *